United States Patent [19]

Baker, Jr. et al.

[11] Patent Number: 4,922,026

[45] Date of Patent: May 1, 1990

[54] ACYLATION PROCESS TO FORM DIKETONES

[75] Inventors: Robert B. Baker, Jr.; R. Garth Pews; Eric W. Otterbacher; James A. Gall, all of Midland, Mich.

[73] Assignee: The Dow Chemical Company, Midland, Mich.

[21] Appl. No.: 290,723

[22] Filed: Dec. 27, 1988

[51] Int. Cl.$^5$ .............................. C07C 45/46
[52] U.S. Cl. .................... 568/322; 568/323
[58] Field of Search ................. 568/323, 322

[56] References Cited

U.S. PATENT DOCUMENTS

| 2,879,296 | 3/1959 | Prill . |
| 2,879,297 | 2/1959 | Prill et al. . |
| 3,065,205 | 11/1962 | Bonner, Jr. . |
| 3,767,289 | 10/1973 | Aviram et al. . |
| 3,883,594 | 5/1975 | Schmerling . |
| 3,907,837 | 9/1975 | Effenberger et al. . |
| 3,953,400 | 1/1976 | Dahl . |
| 3,979,459 | 9/1976 | Rose . |
| 4,025,580 | 8/1977 | Taylor . |
| 4,172,100 | 10/1979 | Tung et al. . |
| 4,172,190 | 10/1979 | Tung et al. . |
| 4,196,154 | 4/1980 | Tung et al. . |
| 4,365,103 | 12/1982 | Chang et al. . |
| 4,487,934 | 1/1984 | Shutske et al. . |

FOREIGN PATENT DOCUMENTS

| 742298 | 5/1970 | Belgium .................. 568/323 |
| 3531837 | 3/1987 | Fed. Rep. of Germany ...... 568/323 |

OTHER PUBLICATIONS

Bayer AG BE-786836-Q.
BASF AG DT-2204973-Q.
U.S.S.R. Science Academy SU-296745-S.
Chemical Abstracts 105:60380v.
Kureha Kagaku Kogyo DE 3620-512-A.
Dow Chemical Company ES 8401-438-A.
Nippon Sheet Glass J61072-727-A.
Sumitomo Chemical NL8101-363.
Zaitsev SU-788-654.
Agence Nat Valorisation DT2726-980.
Pearson, "Friedel-Crafts Acylation With Little Or No Catalyst", *Synthesis*, International Journal of Methods in Synthetic Organic Chemistry, 1972, No. 10, pp. 533-542.
Latterman, "Darstellung Und Charakterisierung Von Einigen Neuen Bis(1-phenylvinyl)-verbingdungen," *Die Makromolykulare Chemie* 17, 175, pp. 2865-2974 (1974).
Schulz et al., "1,3-bis(1-phenylvinyl) Benzene And Its Reactions With Electron Transfer Reagents", *Makromol. Chem.*, 178, 2589-2594 (1977).

*Primary Examiner*—James H. Reamer
*Attorney, Agent, or Firm*—Price, Heneveld, Cooper, DeWitt & Litton

[57] ABSTRACT

Aromatic diketones are prepared by a process comprising contacting at least one acylatable aromatic compound and at least one aromatic diacyl halide in the presence of catalytic amounts of ferric chloride or ferric oxide at an elevated temperature and at superatmospheric conditions.

14 Claims, No Drawings

ACYLATION PROCESS TO FORM DIKETONES

BACKGROUND OF THE INVENTION

The invention relates to a process for acylating benzene, toluene and anisole in the presence of catalytic amounts of ferric chloride. The acylated compounds are particularly useful for the preparation of unsaturated compounds, particularly aromatic dienes, via the Grignard reaction.

Acylation reactions in which the acyl group is introduced by substitution into aliphatic and aromatic compounds are well known in the art. The use of Friedel-Crafts catalysts such as aluminum chloride, ferric chloride and ferric oxide in catalytic amounts, stoichiometric amounts or in excess of stoichiometric amounts for the reaction of aromatic compounds with acyl chlorides, anhydrides or esters is well known. Such acylation reactions are typically effected under reflux at ambient pressure conditions and are often accompanied by poor yields and/or conversions to the desired acylated product.

The acylated products, such as ketones, are desirable intermediates for preparing unsaturated hydrocarbons. A particularly attractive synthesis route for preparing such olefinically unsaturated hydrocarbons is through the Grignard reaction. By this reaction, the acylated compound is reacted with a Grignard reagent. The resulting Grignard reaction product is converted to an alcohol which is separated from its reaction mixture and subsequently dehydrated in the presence of an acid catalyst to form the olefinically unsaturated hydrocarbon.

SUMMARY OF THE INVENTION

The present invention provides a process for the acylation of benzene, toluene and anisole comprising contacting benzene, toluene or anisole with an acylating agent in the presence of at least one Lewis acid catalyst at temperatures in the range of 50° to 300° C. at a pressure in the range of 10 to 1,000 psig.

The process of this invention for the acylation of benzene, toluene and anisole provides significantly higher conversions, yields and selectivities to the desired acylated product in significantly shorter reaction times than is typically required by conventional processes which are effected under reflux at ambient pressure conditions.

PREFERRED EMBODIMENT OF THE INVENTION

In a preferred embodiment of this invention, aromatic diketones are prepared by reacting benzene, toluene or anisole with difunctional acyl halides and anhydrides of aromatic organic acids in the presence of catalytic amounts of ferric chloride at superatmospheric pressures in a temperature range between 50° C. and 300° C.

In accordance with the preferred embodiment of this invention, aromatic diketones having the formula

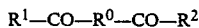

$$R^1-CO-R^0-CO-R^2$$

are prepared by a process comprising contacting benzene, toluene or anisole with an aromatic diacyl halide in the presence of 0.01 to 20, preferably 0.5 to 8, weight percent, based on the weight of the diacyl halide, of ferric chloride or ferric oxide, at a temperature in the range from 50° to 300° C., preferably 100° to 300° C., at a pressure in the range from 10 to 1,000 psig, preferably 100 to 750 psig, with the benzene, toluene or anisole being present in at least a stoichiometric excess, and preferably at a molar ratio of benzene, toluene or anisole:diacyl halide of 2-20:1, preferably 5-12:1; wherein $R^0$ is an aromatic radical having from 6 to 26 nuclear carbon atoms; and $R^1$ and $R^2$ can be the same or different and each is phenyl, methylphenyl or methoxyphenyl. Currently, it is preferred that $R^1$ and $R^2$ are the same and each is methylphenyl or methoxyphenyl.

The compounds which can be acylated, that is, converted to diketones, in accordance with the invention are benzene, toluene and anisole. Currently, the preferred aromatic compounds which are acylated in accordance with this invention are toluene and anisole.

Difunctional acyl halides which can be employed in the practice of the present invention include phthaloyl chloride, isophthaloyl chloride, terephthaloyl chloride, o-xylyl chloride, 1,4-naphthoyl dichloride, anthracene-1,9-diacid chloride, thio-bis(4,4'-benzoyl chloride), benzophenone-4,4'-di(carbonyl chloride), oxy-bis(3,3'-benzoyl chloride), diphenyl-3,3'-(carbonyl chloride), carbonyl-bis(3,3'-benzoyl chloride), sulfonyl-bis(4,4'-benzoyl chloride), sulfonyl-bis(3,3'-benzoyl chloride), sulfonyl-bis(3,4'-benzoyl chloride), thiol-bis(3,4'-benzoyl chloride), diphenyl-3,4'-di(carbonyl chloride), oxy-bis(4,4-2-chlorobenzoyl chloride), naphthalene-1,6-di(carbonyl chloride), naphthalene-2,6-di(carbonyl chloride), oxy-bis(7,7'-naphthalene-2,2'-di(carbonyl chloride)), thiol-bis(8,8'-naphthalene-1,1'-di(carbonyl chloride)), 7,7'-binaphthyl-2,2'-di(carbonyl chloride) and diphenyl-4,4'-di(carbonyl chloride). Currently, isophthaloyl chloride is the acylating agent of choice.

The invention is further illustrated by the following example:

EXAMPLE I

To a mechanically stirred, 600 mL autoclave is added 1 mole of isophthaloyl dichloride, 10 moles of benzene and 2% iron chloride, based on the amount of isophthaloyl dichloride. The reactor is closed and the temperature of the reaction zone is elevated to 200° C. The reaction goes to completion in approximately 4 to5 hours with a quantitative yield of 1,3-phenylene-bis(-phenyl methanone). The maximum pressure experienced during the reaction was 300 psig.

The process of this invention is effected as a batch operation at superatmospheric pressures. The reactants and catalyst are charged to a pressure vessel, such as an autoclave. The autoclave is sealed and heated to the desired temperature and maintained thereat for the desired residence time. At the end of this time, heating is discontinued, the pressure released and the reaction mixture is recovered and purified. Purification includes wiped-film evaporation followed by passage through an activated aluminia column and/or fractional distillation. Alternatively, an inert gas, such as nitrogen, can be introduced into the sealed reactor prior to the heating step.

The embodiments of the invention in which an exclusive property or privilege is claimed are defined as follows:

1. A process for preparing aromatic diketones comprising contacting at least one acylatable aromatic compound selected from the group consisting of benzene, toluene or anisole with at least one aromatic diacyl halide in the presence of a catalytic amount of ferric chloride or ferric oxide at an elevated temperature in the range of 50° to 300° C. and at superatomspheric pressure in the range from 10 to 1,000 psig.

2. A method according to claim 1 wherein said acylatable aromatic compound comprises benzene.

3. A method according to claim 2 wherein said organic diacyl halide comprises isophthaloyl chloride.

4. A process according to claim 1 wherein said acylatable organic compound comprises toluene.

5. A process according to claim 4 wherein said organic diacyl halide comprises isophthaloyl chloride.

6. A process according to claim 1 wherein said acylatable organic compound comprises anisole.

7. A method according to claim 6 wherein said aromatic diacyl halide comprises isophthaloyl chloride.

8. A process according to claim 1 wherein said reaction is effected at a temperature in the range of 50° to 300° C. at a pressure in the range from 100 to 750 psig.

9. A method according to claim 8 wherein said acylatable aromatic compound comprises benzene.

10. A method according to claim 9 wherein said organic diacyl halide comprises isophthaloyl chloride.

11. A process according to claim 8 wherein said acylatable organic compound comprises toluene.

12. A process according to claim 11 wherein said organic diacyl halide comprises isophthaloyl chloride.

13. A process according to claim 9 wherein said acylatable organic compound comprises anisole.

14. A method according to claim 13 wherein said aromatic diacyl halide comprises isophthaloyl chloride.

* * * * *